United States Patent [19]
Elokdah et al.

[11] Patent Number: 5,554,607
[45] Date of Patent: Sep. 10, 1996

[54] USE OF 2-THIOXO-IMIDAZOLIN-4-ONE DERIVATIVES IN THE TREATMENT OF ATHEROSCLEROSIS

[75] Inventors: Hassan M. Elokdah, Fairless Hills, Pa.; Sie-Yearl Chai, Lawrenceville, N.J.; Theodore S. Sulkowski, Wayne; Donald P. Strike, St. Davids, both of Pa.

[73] Assignee: American Home Products Corporation, Madison, N.J.

[21] Appl. No.: 563,325

[22] Filed: Nov. 28, 1995

[51] Int. Cl.⁶ .................. A61K 31/395; A61K 31/55; A61K 31/445; A61K 31/44

[52] U.S. Cl. .................. 514/210; 514/212; 514/326; 514/341; 514/422; 514/430; 514/431; 514/432; 514/444; 514/449; 514/450; 514/451; 514/461; 514/824

[58] Field of Search .................. 514/210, 212, 514/326, 341, 422, 430, 431, 432, 444, 449, 450, 451, 461, 824

[56] References Cited

U.S. PATENT DOCUMENTS

| | | | |
|---|---|---|---|
| 5,137,904 | 8/1992 | Baran et al. | 514/389 |
| 5,411,981 | 5/1995 | Gaillard-Kelly et al. | 514/386 |

FOREIGN PATENT DOCUMENTS

| | | |
|---|---|---|
| 0578516 | 1/1994 | European Pat. Off. . |
| 0584694 | 3/1994 | European Pat. Off. . |
| 4887030 | of 1973 | Japan . |
| 4297461 | of 1992 | Japan . |
| 9318057 | 9/1993 | WIPO . |
| 9420460 | 9/1994 | WIPO . |

Primary Examiner—Kimberly Jordan
Attorney, Agent, or Firm—Richard K. Jackson

[57] ABSTRACT

A method for increasing the HDL cholesterol concentration in the blood of a mammal in need of increased HDL cholesterol blood concentration, which comprises administering to said mammal, orally or parenterally, a compound of formula I:

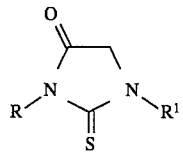

wherein R is alkyl; a substituted or unsubstituted aromatic N, O or S heterocycle; substituted or unsubstituted aryl, arylalkyl, benzhydryl or indanyl, in which the substituents are one to three members independently selected from the group consisting of alkyl, alkoxy, alkylthio, alkenyl, alkynyl, halo, perfluoroalkyl, perfluoroalkyl or hydroxy; and $R^1$ is aryl, alkyl, alkenyl, alkynyl or substituted aryl where the substituents are one to three members independently selected from the group consisting of alkyl, alkoxy, alkylthio, alkenyl, alkynyl, halo, perfluoroalkyl, perfluoroalkoxy or hydroxy.

36 Claims, No Drawings

USE OF 2-THIOXO-IMIDAZOLIN-4-ONE DERIVATIVES IN THE TREATMENT OF ATHEROSCLEROSIS

BACKGROUND OF INVENTION

Numerous studies have demonstrated that both the risk of coronary heart disease (CHD) in humans and the severity of experimental atherosclerosis in animals are inversely correlated with serum HDL cholesterol (HDL-C) concentrations (Russ et al, Am. J. Mede, 11 (1951) 480–493; Gofman et al, Circulation, 34 (1966) 679–697; Miller and Miller, Lancet, 1 (1975) 16–19; Gordon et al, Circulation, 79 (1989) 8–15; Stampfer et al, N. Engl. J. Med., 325 (1991) 373–381; Badimon et al, Lab. Invest., 60 (1989) 455–461 ). Atherosclerosis is the process of accumulation of cholesterol within the arterial wall which results in the occlusion, or stenosis, of coronary and cerebral arterial vessels and subsequent myocardial infarction and stroke. Angiographical studies have shown that elevated levels of some HDL particles appears to be correlated with a decrease in the number of sites of stenosis in the coronary arteries of humans (Miller et al, Br. Med. J., 282 (1981) 1741–1744).

There are several mechanisms by which HDL may protect against the progression of atherosclerosis. Studies in vitro have shown that HDL is capable of removing cholesterol from cells (Picardo et al, Arteriosclerosis, 6 (1986) 434–441). Data of this nature suggests that one antiatherogenic property of HDL may lie in its ability to deplete tissues of excess free cholesterol and eventually lead to the delivery of this cholesterol to the liver (Glomset, J. Lipid Res., 9 (1968) 155–167). This has been supported by experiments showing efficient transfer of cholesterol from HDL to the liver (Glass et al, Circulation, 66 (Suppl. I) (1982) 102; MacKinnon et al, J. Biol. Chem., 261 (1986) 2548–2552). In addition, HDL may serve as a reservoir in the circulation for apoproteins necessary for the rapid metabolism of triglyceride-rich lipoproteins (Grow and Fried, J. Biol. Chem., 253 (1978) 1834–1841; Lagocki and Scanu, J. Biol. Chem., 255 (1980) 3701–3706; Schaefer et al, J. Lipid Res., 23 (1982) 1259–1273). Accordingly, agents which increase HDL cholesterol concentrations are useful as anti-atherosclerotic agents, particularly in the treatment of dyslipoproteinemias and coronary heart disease.

U.S. Pat. No. 5,137,904 discloses a group of thiohydantoin derivatives of the formula

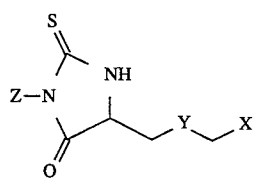

which Z is alkyl, phenylalkyl, phenyl or substituted phenyl, where the substituent is a halogen, alkyl, alkoxy or halogenated alkyl group; X is phenyl, halophenyl, alkyl, alkenyl, or alkynyl; and Y is S or O. These compounds inhibit collagen-induced and ADP-induced platelet aggregation.

EP 0584694 and WO 93/18057 disclose a group of imidazolidin-3-yl benzoyl or alkanoyl amino acid derivatives as inhibitors of cell-cell adhesion for use in inhibition of thrombocyte aggregation, metastasis and osteoclast formation. Chronic administration for prevention of arteriosclerosis and thrombosis is disclosed.

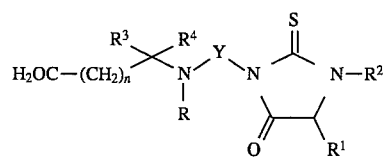

in which $Y=-(CH_2)_n-CO-$ or $-Ph-CO-$.

JP 04,297,461 discloses a group of 2-thiohydantoin compounds of the following formula, said to be useful as anti-bacterial, anti-viral, anti-inflammatory and anti-rheumatic agents:

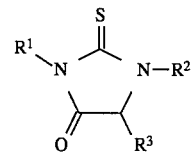

where $R^1$ is lower alkyl, lower alkenyl, phenyl(lower)alkyl or substituted phenyl with 1–3 groups chosen from lower alkyl, lower alkoxy, halogen, lower alkoxycarbonyl or hydroxy;

$R^2$ is either hydrogen or alkanoyl; and $R^3$ is hydrogen, lower alkyl, phenyl, phenyl (lower) alkyl, or a lower alkylthio, lower alkyl group that can be substituted with one to three phenyl groups that have had a lower alkoxy group.

EP 0578516 discloses a group of 2-thiohydantoins, said to be useful anti-androgenic agents for treatment of various cancer, of the formula:

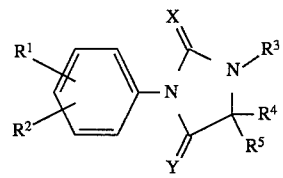

where X is oxygen or sulfur;

Y is oxygen, sulfur or NH $R^1$ and $R^2$ are cyano, nitro, halogen, trifluoromethyl, or a free or esterified carboxylic acid or salt;

$R^3$ is hydrogen, alkyl, alkenyl, alkynyl, aryl or aryl-alkyl;

$R^4$ and $R^5$ are hydrogen, optionally substituted alkyl, or cycloalkyl.

U.S. Pat. No. 5,411,981 discloses compounds closely related to EP 0578516, supra, where $R^4$ and $R^5$ are both methyl.

U.S. Pat. No. 3,923,994 discloses a group of 3-aryl-2-thiohydantoin derivatives of the following formula, which have anti-arthritic activity:

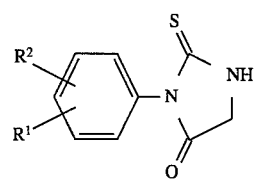

where $R^1$ and $R^2$ are hydrogen, chloro, bromo, fluoro or alkyl of 1–2 carbon atoms.

JP 73 87,030 discloses a group of 3-phenyl-2-thiohydantoin derivatives useful as herbicides.

U.S. Pat. No. 4,473,393 discloses a group of pesticidal thiohydantoin compositions.

DESCRIPTION OF INVENTION

In accordance with this invention there is provided a method for increasing HDL cholesterol concentration in the blood of a mammal, which comprises administering to said mammal an amount of a substituted 2-thioxo-imidazolidin-4-one sufficient to increase that HDL cholesterol concentration, said substituted 2-thioxo-imidazolidin-4-one being a compound of formula I:

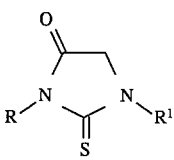

wherein

R is alkyl of 1 to 6 carbon atoms; a substituted or unsubstituted aromatic N, O or S heterocycle having 4 to 6 carbon and one hetero ring members; substituted or unsubstituted aryl of 6 to 10 carbon atoms, arylalkyl of 7 to 12 carbon atoms, benzhydryl or indanyl, in which the substituents are one to three members independently selected from the group consisting of alkyl of 1 to 6 carbon atoms, alkoxy of 1 to 6 carbon atoms, alkylthio of 1 to 6 carbon atoms, alkenyl of 2 to 6 carbon atoms, alkynyl of 2 to 6 carbon atoms, halo, perfluoroalkyl of 1 to 6 carbon atoms, perfluoroalkoxy of 1 to 6 carbon atoms or hydroxy; and $R^1$ is aryl of 6 to 10 carbon atoms, alkyl of 1 to 6 carbon atoms, alkenyl of 2 to 6 carbon atoms, alkynyl of 2 to 6 carbon atoms or substituted aryl of 6 to 10 carbon atoms where the substituents are one to three members independently selected from the group consisting of alkyl of 1 to 6 carbon ate,ms, alkoxy of 1 to 6 carbon atoms, alkylthio of 1 to 6 carbon atoms, alkenyl of 2 to 6 carbon atoms, alkynyl of 2 to 6 carbon atoms, halo, perfluoroalkyl of 1 to 6 carbon atoms, perfluoroalkoxy of 1 to 6 carbon atoms or hydroxy.

A preferred method employs a compound of formula I in which R is substituted phenyl where the substituents are two members of the group consisting of alkyl of 1 to 6 carbon atoms, perfluoroalkoxy of 1 to 6 carbon atoms, halo, or ortho substituted trimethylene or tetramethylene and $R^1$ is alkyl of 1 to 6 carbon atoms, alkenyl of 2 to 6 carbon atoms or alkynyl of 2 to 6 carbon atoms.

Another preferred method involves the administration of a compound of formula I in which R is substituted phenyl where the substituents are a halo and an alkyl group of 1 to 3 carbon atoms or ortho substituted trimethylene and $R^1$ is alkyl of 1 to 3 carbon atoms, alkenyl of 2 to 4 carbon atoms or alkynyl of 2 to 4 carbon atoms.

A more preferred method results from the administration of a compound of formula I in which R is substituted phenyl where the substituents are chloro or fluoro in the 4- or 5-position and an alkyl group of 1 to 3 carbon atoms and R 1 is alkyl of 1 to 3 carbon atoms, alkenyl of 2 to 4 carbon atoms or alkynyl of 2 to 4 carbon atoms.

The most preferred compounds of this invention based upon there potency and overall activity profile in the standard experimental test model are:

3-(5-Chloro-2-methylphenyl)-1-methyl-2-thioxo-imidazolidin-4-one
3-(3-Chloro-2-methylphenyl)-1-methyl-2-thioxo-imidazolidin-4-one
3-(4-Chloro-2-methylphenyl)-1-methyl-2-thioxo-imidazolidin-4-one
3-(Indan-5-yl)- 1-methyl-2-thioxo-imidazolidin-4-one
3-(2,6-Diisopropylphenyl)-1-methyl-2-thioxo-imidazolidin-4-one
3-(2-Ethyl-6-isopropylphenyl)-1-methyl-2-thioxo-imidazolidin-4-one
3-(2-Ethyl-6-methylphenyl)-1-methyl-2-thioxo-imidazolidin-4-one
3-(5-Chloro-2-methylphenyl)-1-ethyl-2-thioxo-imidazolidin-4-one
3-(2,6-Dichlorophenyl)-1-ethyl-2-thioxo-imidazolidin-4-one
1-Ethyl-3-(4-fluorophenyl)-2-thioxo-imidazolidin-4-one
1-Ethyl-2-thioxo-3-(4-trifluoromethoxyphenyl)-imidazolidin-4-one
3-(2,6-Dimethylphenyl)-1-ethyl-2-thioxo-imidazolidin-4-one
1-Ethyl-3-isobutyl-2-thioxo-imidazolidin-4-one
3-(2-Chlorophenyl)-1-ethyl-2-thioxo-imidazolidin-4-one
1-Ethyl-3-(2-tolyl)-2-thioxo-imidazolidin-4-one
3-(2-Chloro-6-methylphenyl)-1-ethyl-2-thioxo-imidazolidin-4-one
1-Ethyl-3-(5-fluoro-2-methylphenyl)-2-thioxo-imidazolidin-4-one
3-(2,6-Diisopropylphenyl)-1-ethyl-2-thioxo-imidazolidin-4-one
1-Ethyl-2-thioxo-3-(2-trifluoromethylphenyl)-imidazolidin-4-one
1-Ethyl-3-(2-ethyl-6-methylphenyl)-2-thioxo-imidazolidin-4-one
3-(2-Chloro-4-methylphenyl)-1-ethyl-2-thioxo-imidazolidin-4-one
3-(2,4-Dichlorophenyl)-1-ethyl-2-thioxo-imidazolidin-4-one
3-(2,4-Dimethylphenyl)-1-ethyl-2-thioxo-imidazolidin-4-one
3-(2,5-Dimethylphenyl)-1-ethyl-2-thioxo-imidazolidin-4-one
1-Ethyl-2-thioxo-3-(2,4,5-trimethylphenyl)-imidazolidin-4-one
1-Ethyl-3-(2-isopropylphenyl)-2-thioxo-imidazolidin-4-one
1-Ethyl-3-(2-ethylphenyl)-2-thioxo-imidazolidin-4-one
3-(5-Chloro-2-methylphenyl)-1-phenyl-2-thioxo-imidazolidin-4-one
3-(5-Chloro-2-methylphenyl)-1-isopropyl-2-thioxo-imidazolidin-4-one
3-(2,6-Dimethylphenyl)-1-isopropyl-2-thioxo-imidazolidin-4-one
3-(2-Ethyl-6-methylphenyl)-1-isopropyl-2-thioxo-imidazolidin-4-one
1-Butyl-3-(4-fluorophenyl)-2-thioxo-imidazolidin-4-one
1-Allyl-3-(2,6-dimethylphenyl)-2-thioxo-imidazolidin-4-one
3-(2,6-Dimethylphenyl)-1-(prop-2-ynyl)-2-thioxo-imidazolidin-4-one
3-(3-Chloro-4-methylphenyl)-1-methyl-2-thioxo-imidazolidin-4-one
3-(2-Ethylphenyl)-1-methyl-2-thioxo-imidazolidin-4-one
1-Methyl-3-(2-isopropylphenyl)-2-thioxo-imidazolidin-4-one
3-(4-t-Butylphenyl)-1-methyl-2-thioxo-imidazolidin-4-one
1-Allyl-3-(5-chloro-2-methylphenyl)-2-thioxo-imidazolidin-4-one
3-(5-Chloro-2-methylphenyl )-1-(prop-2-ynyl)-2-thioxo-imidazolidin-4-one
1-Ethyl-3-(2-ethyl-6-isopropylphenyl)-2-thioxo-imidazolidino4-one.

The compounds of the invention can be prepared readily according to the following reaction scheme or modification thereof using readily available starting materials, reagents and conventional synthetic procedures. It is also possible to make use of variants of these process steps, which in themselves are known to and well within the preparatory skill of the medicinal chemist. In the following reaction scheme, $R^2$ is hydrogen or alkyl of 1 to 6 carbon atoms and X is a halogen.

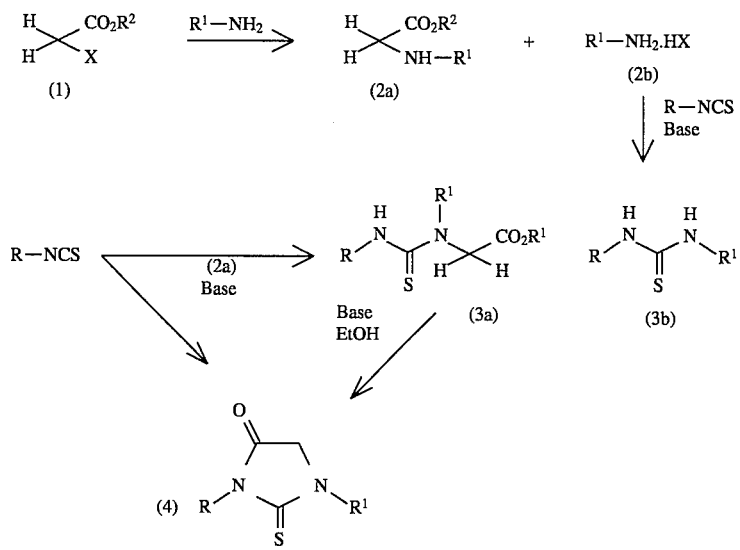

N-Substituted amino acids (2a) were prepared by reacting the corresponding a-halo acids (1) with the appropriate amines (excess). The reaction was carried out either neat or in water at ambient temperature for 18 hours. One equivalent of the amine scavenges the hydrohalide formed during the alkylation forming the amine hydrohalide (2b) as a side product. The N-alkyl amino acids (2a) were either purified by crystallization from an appropriate solvent, or reacted with the isothiocyanates as crude product mixtures containing the amine hydrohalide salt. Reaction of 2a with isothiocyanates is carried out in chloroform or methylene chloride in the presence of a base such as triethyl amine. The mixture is heated at reflux for 3 to 18 hours. The reaction affords either the thiourea (3a) or the thiohydantoin (4) directly (depending on the nature of $R^1$). Cyclization of 3a to the thiohydantoin (4) is accomplished by refluxing in ethanol for 2 to 3 hours in the presence of base (triethyl amine). In the case of reacting the crude product mixture (2a & 2b) with isothiocyanates, the thiourea (3b) is formed as a side product along with 4. Purification of 4 was achieved by 1) fractional crystallization, 2) flash chromatography, 3) extracting 3b in 2N hydrochloric acid or 4) precipitating 3b as its hydrochloride salt from an appropriate solvent such as ethyl acetate or diethyl ether.

This invention also provides pharmaceutical compositions comprised of the 2-thioxo imidazolidin-4-one derivatives either alone or in combination with excipients (i.e. pharmaceutically acceptable materials with no pharmacological effects). Such compositions are useful in the treatment of atherosclerotic conditions such as dyslipoproteinemias and coronary heart disease, in that they increase the blood serum high density lipoprotein concentration of mammals treated with the compounds.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure stroke, peripheral arterial occlusion, and related disease states). These measures will slow the rate of progress of the disease state and assist the body in reversing the process direction in a natural manner.

Any suitable carder known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carder is a finely divided solid which is in admixture with the finely divided active ingredient. In tablets the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carder is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions which are sterile solutions or suspensions can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of HDL and the patients symptomatic relief analysis may be used to determine whether a larger dose is indicated. Based upon the data presented below, the projected daily dose for both human and veterinary use will be from about 10 to about 200 milligrams/kilogram per day. However, in general, satisfactory results are indicated to be obtained at daily dosages in the range of from 400 milligrams to about 2000 milligrams, conveniently administered in divided doses two to four times a day.

The ability of the compounds of this invention to increase blood serum HDL levels was established by the following standard experimental procedure for determination of HDL cholesterol:

Male Sprague-Dawley rats weighing 200–225 g are housed two per cage and fed Purina Rodent Chow Special Mix 5001-S supplemented with 0.25% cholic acid and 1.0% cholesterol and water ad libitum for 8 days. Each test substance is administered to a group of six rats fed the same diet with the test diet mixed in as 0.005 –0.1% of the total diet. Body weight and food consumption are recorded prior to diet administration and at termination. Typical doses of the test substances are 5–100 mg/kg/day.

At termination, blood is collected from anesthetized rats and the serum is separated by centrifugation. Total serum cholesterol is assayed using the Sigma Diagnostics enzymatic kit for the determination of cholesterol, Sigma Procedure No. 352, modified for use with ninety-six well microliter plates. After reconstitution with water the reagent contains 300 U/l cholesterol oxidase, 100 U/l cholesterol esterase, 1000 U/l horse radish peroxidase, 0.3 mmoles/l 4-aminoantipyrine and 30.0 mmoles/l p-hydroxybenzenesulfonate in a pH 6.5 buffer. In the reaction cholesterol is oxidized to produce hydrogen peroxide which is used to form a quinoneimine dye. The concentration of dye formed is measured spectrophotometrically by absorbance at 490 nm after incubation at 25C. for 30 minutes. The concentration of cholesterol was determined for each serum sample relative to a commercial standard from Sigma.

HDL cholesterol concentrations in serum are determined by separation of lipoprotein classes by fast protein liquid chromatography (FPLC) by a modification of the method of Kieft et al., *J. Lipid Res.*, 32 (1991) 859–866. 25 ul of serum is injected onto Superose 12 and Superose 6 (Pharmacia), in series, with a column buffer of 0.05 M Tris (2-amino-2-hydroxymethyl-1,3-propanediol) and 0.15M sodium chloride at a flow rate of 0.5 ml/min. The eluted sample is mixed on line with Boehringer-Mannheim cholesterol reagent pumped at 0.2 ml/min. The combined eluents are mixed and incubated on line through a knitted coil (Applied Biosciences) maintained at a temperature of 45C. The eluent is monitored by measuring absorbance at 490 nm and gives a continuous absorbance signal proportional to the cholesterol concentration. The relative concentration of each lipoprotein class is calculated as the percent of total absorbance. HDL cholesterol concentration, in serum, is calculated as the per cent of total cholesterol as determined by FPLC multiplied by the total serum cholesterol concentration.

Test compounds were administered at a dose of 100 mg/kg. The duration of treatment was eight days. The compounds of the present invention increase HDL cholesterol concentrations as summarized in Table I:

TABLE 1

| Compound of Example | HDL Cholesterol Level Increase (%) |
| --- | --- |
| 1 | 159 |
| 2 | 57 |
| 3 | 29 |
| 4 | 39 |
| 5 | 150 |
| 6 | 101 |
| 7 | 202 |
| 8 | 112 |
| 9 | 89 |
| 10 | 141 |
| 11 | 203 |
| 12 | 84 |
| 13 | 222 |
| 14 | 203 |
| 15 | 92 |
| 16 | 132 |
| 17 | 142 |
| 18 | 59 |
| 19 | 39 |
| 20 | 265 |
| 21 | 180 |
| 22 | 26 |
| 23 | 95 |
| 24 | 157 |
| 25 | 163 |
| 26 | 65 |
| 27 | 222 |
| 28 | 112 |
| 29 | 54 |
| 30 | 115 |
| 31 | 167 |
| 32 | 112 |
| 33 | 66 |
| 34 | 49 |
| 35 | 98 |
| 36 | 30 |
| 37 | 49 |
| 38 | 83 |
| 39 | 124 |
| 40 | 112 |
| 41 | 202 |
| 42 | 237 |
| 43 | 78 |
| 44 | 39 |
| 45 | 127 |
| 46 | 146 |
| 47 | 24 |
| 48 | 64 |
| 49 | 52 |
| 50 | 77 |
| 51 | 88 |
| 52 | 100 |
| 53 | 47 |
| 54 | 71 |
| 55 | 87 |
| 56 | 53 |
| 57 | 183 |
| 58 | 62 |
| 59 | 177 |

TABLE 1-continued

| Compound of Example | HDL Cholesterol Level Increase (%) |
|---|---|
| 60 | 74 |
| 61 | 325 |
| 62 | 204 |
| 63 | |

The following examples are presented to illustrate the production of representative compounds useful in the method of this invention, rather than as a limit to the scope of applicant's invention:

EXAMPLE 1

3-(5-Chloro-2-methylphenyl)-1-methyl-2-thioxo-imidazolidin-4-one

A mixture of sarcosine ethyl ester hydrochloride (7.68 g), 5-chloro-2-methylphenyl-isothiocyanate (9.18 g), triethyl amine (12 g) and chloroform (200 mL) was heated at reflux for 5 hours. The mixture was cooled to ambient temperature, washed with 1N HCl (2×200 mL), then with water (200 mL) The organic phase was evaporated to dryness. The residue was crystallized from ethanol to give the title compound (9.2 g) as a tan solid, m.p. 132°–134° C. Anal. Calcd. for $C_{11}H_{11}Cl\ N_2O\ S$: C, 51.87; H, 4.35; N, 11.00. Found: C, 51.79; H, 4.12; N, 10.73. Mass spectrum (EI, M.$^+$) m/z 254/256.

EXAMPLE 2

3-Benzhydryl-1-methyl-2-thioxo-imidazolidin-4-one

The title compound was prepared by the procedure described in Example 1 using 11.25 g of benzhydryl-isothiocyanate, 7.68 g of sarcosine ethyl ester hydrochloride, 12 g of triethyl amine, and 200 mL of chloroform. The title compound was obtained (7.40 g) as an off-white solid, m.p. 139°–141° C. Anal. Calcd. for $C_{17}H_{16}N_2O\ S$: C, 68.89; H, 5.44; N, 9.45. Found: C, 68.92; H, 5.43; N, 9.58. Mass spectrum (EI, M.$^+$) m/z 296.

EXAMPLE 3

1-Methyl-3-(pyridin-3-yl)-2-thioxo-imidazolidin-4-one

A mixture of sarcosine ethyl ester hydrochloride (7.68 g), pyridin-3-yl-isothiocyanate (6.8 g), triethyl amine (10.1 g) and chloroform (200 mL) was heated at reflux for 3.5 hours. The solvent was evaporated. The residue was dissolved in ethyl acetate (300 mL) and washed with water (2×200 mL). The organic phase was dried over anhydrous magnesium sulfate. The solvent was evaporated. Crystallization from ethyl acetate afforded the title compound (4.1 g) as an off-white solid, m.p. 149°–151° C. Anal. Calcd. for $C_9H_9N_3O\ S$: C, 52.16; H, 4.38; N, 20.28. Found: C, 52.16; H, 4.05; N, 20.06. Mass spectrum (EI, M.$^+$) m/z 207.

EXAMPLE 4

3-(5-Chloro-2-methoxyphenyl-1-methyl-2-thioxo-imidazolidin-4-one

A mixture of sarcosine ethyl ester hydrochloride (7.68 g), 5-chloro-2-methoxyphenyl-isothiocyanate (10.0 g), triethylamine (10.0 g) and chloroform (150 mL) was heated at reflux for 4.5 hours. The mixture was cooled to ambient temperature. The precipitated solid was collected, washed with chloroform and air dried to give the title compound (11.8 g) as an off-white solid, m.p. 245°–247° C. Anal. Calcd. for $C_{11}H_{11}Cl\ N_2\ O\ S$: C, 48.80; H, 4.10; N,10.35. Found: C, 48.42; H, 3.96; N, 10.33. Mass spectrum (EI, M.$^+$) m/z 270.

EXAMPLE 5

3-(3-Chloro-2-methylphenyl)-1-methyl-2-thioxo-imidazolidin-4-one

The title compound was prepared by the procedure described in Example 1 using 13.2 g of 3-chloro-2-methylphenyl-isothiocyanate, 11.0 g of sarcosine ethyl ester hydrochloride, 25 g of triethyl amine, and 300 mL of chloroform. Crystallization from diethyl ether afforded the title compound (15.2 g) as a tan solid, m.p. 122°–124° C. Anal. Calcd. for $C_{11}H_{11}Cl\ N_2O\ S$: C, 51.87; H, 4.35; N,11.00. Found: C, 51.96; H, 4.21; N, 11.05. Mass spectrum (EI, M.$^+$) m/z 254/256.

EXAMPLE 6

3-(3-Chloro-4-methylphenyl)-1-methyl-2-thioxo-imidazolidin-4-one

The title compound was prepared by the procedure described in Example 1 using 18.3 g of 3-chloro-4-methylphenyl-isothiocyanate, 15.3 g of sarcosine ethyl ester hydrochloride, 25 g of triethyl amine, and 300 mL of chloroform. Crystallization from ethyl acetate afforded the title compound (14.5 g) as an off-white solid, m.p. 178°–180° C. Anal. Calcd. for $C_{11}H_{11}Cl\ N_2O\ S$: C, 51.87; H, 4.35; N,11.00. Found: C, 1.89; H, 4.20; N, 10.95. Mass spectrum (+FAB, [M+H]$^+$) m/z 255/257.

EXAMPLE 7

3-(4-Chloro-2-methylphenyl)-1-methyl-2-thioxo-imidazolidin-4-one

The title compound was prepared by the procedure described in Example 1 using 9.18 g of 4-chloro-2-methylphenyl-isothiocyanate, 7.68 g of sarcosine ethyl ester hydrochloride, 12.0 g of triethyl amine, and 300 mL of chloroform. Crystallization from diethyl ether afforded the title compound (7.5 g) as an off-white solid, m.p. 113°–115° C. Anal. Calcd. for $C_{11}H_{11}Cl\ N_2O\ S$: C, 51.87; H, 4.35; N,11.00. Found: C, 51.72; H, 4.17; N, 10.88. Mass spectrum (EI, M.$^+$) m/z 254/256.

EXAMPLE 8

3-(Indan-5-yl)-1-methyl-2-thioxo-imidazolidin-4-one

The title compound was prepared by the procedure described in Example 1 using 7.7 g of indan-5-yl-isothiocyanate, 6.7 g of sarcosine ethyl ester hydrochloride, 12 g of triethyl amine, and 300 mL of chloroform. Crystallization from ethyl acetate afforded the title compound (7.9 g) as a tan solid, m.p. 158–160° C. Anal. Calcd. for $C_{13}H_{14}N_2O\ S$: C, 63.39; H, 5.73; N,11.37. Found: C, 63.30; H, 5.81; N, 11.31. Mass spectrum (EI, M.$^+$) m/z 246.

EXAMPLE 9

3-(2,6-Diisopropylphenyl)-1-methyl-2-thioxo-imidazolidin-4-on.

The title compound was prepared by the procedure described in Example 1 using 8.3 g of 2,6-diisopropylphenyl-isothiocyanate, 5.8 g of sarcosine ethyl ester hydrochloride, 14.5 g of triethyl amine, and 200 mL of chloroform. Crystallization from diethyl ether/hexane mixture afforded the title compound (6.6 g) as a tan solid, m.p. 174°–176° C. Anal. Calcd. for $C_{16} H_{22} N_2O$ S: C, 66.17; H, 7.63; N, 9.64. Found: C, 66.39; H, 7.63; N, 9.59. Mass spectrum (+FAB, $[M+H]^+$) m/z 269/271.

EXAMPLE 10

3-(2-Ethyl-6-isopropylphenyl)-1-methyl-2-thioxo-imidazolidin-4-one

The title compound was prepared by the procedure described in Example 1 using 10.25 g of 2-ethyl-6-isopropylphenyl-isothiocyanate, 7.68 g of sarcosine ethyl ester hydrochloride, 14.8 g of triethyl amine, and 200 mL of chloroform. Crystallization from diethyl ether/hexane mixture afforded the title compound (8.95 g) as a tan solid, m.p. 132°–134° C. Anal. Calcd. for $C_{15} H_{20} N_2O$ S: C, 65.18; H, 7.29; N, 10.13. Found: C, 65.11; H, 7.31; N, 10.05. Mass spectrum (PBEI, $M.^+$) m/z 276.

EXAMPLE 11

3-(2-Ethyl-6-methylphenyl)-1-methyl-2-thioxo-imidazolidin-4-one

The title compound was prepared by the procedure described in Example 1 using 8.9 g of 2-ethyl-6-methylphenyl-isothiocyanate, 7.68 g of sarcosine ethyl ester hydrochloride, 12.5 g of triethyl amine, and 250 mL of chloroform. Crystallization from diethyl ether afforded the title compound (7.45 g) as a peach solid, m.p. 106°–108° C. Anal. Calcd. for $C_{13} H_{16} N_2O$ S: C, 62.87; H, 6.49; N, 11.28. Found: C, 62.52; H, 6.61; N, 11.29. Mass spectrum (+ESI, $[M+H]^+$) m/z 269/271.

EXAMPLE 12

3-(2-Chloro-6-methylphenyl)-1-methyl-2-thioxo-imidazolidin-4-one

The title compound was prepared by the procedure described in Example 1 using 9.2 g of 2-chloro-6-methylphenyl-isothiocyanate, 7.68 g of sarcosine ethyl ester hydrochloride, 12 g of triethyl amine, and 200 mL of chloroform. Crystallization from ethanol afforded the title compound (7.1 g) as an orange solid (7.1 g), m.p. 142°–145° C. Anal. Calcd. for. $C_{11} H_{11} N_2 O$ S: C, 51.87; H, 4.35; N,11.00. Found: C, 51.96; H, 4.26; N, 10.97. Mass spectrum (El, $M.^+$) m/z 254.

EXAMPLE 13

3-(2-Ethylphenyl)-1-methyl-2-thioxo-imidazolidin-4-one

The title compound was prepared by the procedure described in Example 1 using 16.3 g of 2-ethylphenyl-isothiocyanate, 15.3 g of sarcosine ethyl ester hydrochloride, 20.2 g of triethyl amine, and 300 mL of chloroform. The title compound (20.4 g) was obtained as an off-white solid, m.p. 135°–137° C. Anal. Calcd. for $C_{12} H_{14} N_2O$ S: C, 61.51; H, 6.02; N,11.96. Found: C, 61.11; H, 5.92; N, 11.71. Mass spectrum (El, $M.^+$) m/z 234.

EXAMPLE 14

1-Methyl-3-(2-isopropylphenyl)-2-thioxo-imidazolidin,4-one

The title compound was prepared by the procedure described in Example 1 using 14.2 g of 2-isopropylphenyl-isothiocyanate, 12.29 g of sarcosine ethyl ester hydrochloride, 16.0 g of triethyl amine, and 200 mL of chloroform. Crystallization from diethyl ether afforded the title compound (15.9 g) as a peach solid, m.p. 129°–131° C. Anal. Calcd. for $C_{13} H_{16} N_2O$ S: C, 62.87; H, 6.49; N, 11.28. Found: C, 62.89; H, 6.38; N, 11.28. Mass spectrum (EI, $M.^+$) m/z 248.

EXAMPLE 15

3-(2,6-Dichlorophenyl)-1-methyl-2-thioxo-imidazolidin-4-one

The title compound was prepared by the procedure described in Example 1 using 14.28 g of 2,6-dichlorophenyl-isothiocyanate, 10.75 g of sarcosine ethyl ester hydrochloride, 14.5 g of triethyl amine, and 200 mL of chloroform. Crystallization from diethyl ether afforded the title compound (16.9 g) as a light peach solid, m.p. 207°–209° C. Anal. Calcd. for $C_{10} H_8 C_{12} N_2O$ S: C, 43.65; H, 2.93; N, 10.18. Found: C, 43.57; H, 2.61; N, 10.14. Mass spectrum (El, $M.^+$) m/z 274.

EXAMPLE 16

3-(5-Chloro-2-methylphenyl)-1-ethyl-2-thioxo-imidazolidin-4-one

2-Chloro acetic acid (27.5 g) was added portionwise while stirring to a 70% aqueous ethyl amine solution (500 mL). The addition was carded over a period of 30 minutes. The mixture was stirred at ambient temperature for 18 hours. The mixture was then evaporated to a viscous oily residue (55 g). The crude product consisted of a 1:1 mixture of N-ethyl glycine and ethyl amine hydrochloride. This product mixture was used without further purification for the preparation of the title compound, in the next paragraph, and for preparation of the title compounds described in Example 17 through Example 42 and in Example 58.

A mixture of the crude N-ethyl glycine (9.23 g), 5-chloro-2-methylphenylisothiocyanate (9.18 g), triethyl amine (10 g) and chloroform (250 mL) was heated at reflux for 18 hours. The solvent was evaporated. The residue was dissolved in ethyl acetate (400 mL) and water (300 mL). The organic phase was washed with 1N HCl (2×300 mL), then evaporated to dryness. Purification was achieved through crystallization from ethanol. The title compound (7.6 g) was obtained as a light pink solid, m.p. 152°–154° C. Anal. Calcd. for. $C_{12} H_{13} Cl N_2O$ S: C, 53.63; H, 4.88; N, 10.42. Found: C, 53.36; H, 4.79; N, 10.35. Mass spectrum (EI, $M.^+$) m/z 268/270.

EXAMPLE 17

3-(2,6-Dichlorophenyl)-1-ethyl-2-thioxo-imidazolidin-4-one

The title compound was prepared by the procedure described in Example 16 using 10.2 g of 2,6-dichlorophenyl-isothiocyanate, 7.4 g of N-ethyl glycine, 10 g of triethyl amine, and 250 mL of chloroform. Purification was achieved through crystallization from ethanol. The title compound (6.5 g) was obtained as a tan solid, m.p. 170°–172° C. Anal. Calcd. for. $C_{11} H_{10} Cl_2 N_2 O S$: C, 45.69; H, 3.48; N, 9.69. Found: C, 45.53; H, 3.19; N, 9.62. Mass spectrum (EI, M.$^+$) m/z 288/290/292.

EXAMPLE 18

1-Ethyl-3-(4-fluorophenyl)-2-thioxo-imidazolidin-4-one

The title compound was prepared by the procedure described in Example 16 using 7.65 g of 4-fluorophenyl-isothiocyanate, 9.32 g of N-ethyl glycine, 10 g of triethyl amine, and 250 mL of chloroform. Purification was achieved through crystallization from ethanol. The title compound (6.6 g) was obtained as a pink solid, m.p. 149°–151° C. Anal. Calcd. for. $C_{11} H_{11} F N_2 O S$: C, 55.45; H, 4.65; N, 11.76. Found: C, 55.31; H, 4.51; N, 10.82. Mass spectrum (EI, M.$^+$) m/z 238.

EXAMPLE 19

3-(5-Chloro-2-methoxyphenyl)-1-ethyl-2-thioxo-imidazolidin-4-one

A mixture N-ethyl glycine (9.2 g), 5-chloro-2-methoxyphenyl-isothiocyanate (10 g), triethylamine (10.1 g), methylene chloride (150 mL) was heated at reflux for 3.5 hours. The mixture was evaporated to dryness. The residue collected, washed with hot ethanol and dried. Title compound (7.6 g) was obtained as a creamy solid, m.p. 171°–174° C. Anal. Calcd. for. $C_{12} H_{13} Cl N_2 O_2 S$: C, 50.61; H, 4.60; N, 9.84. Found: C, 50.33; H, 4.50; N, 9.69. Mass spectrum (EI, M.$^+$) m/z 284/286.

EXAMPLE 20

1-Ethyl-2-thioxo-3-(4-trifluoromethoxyphenyl)-imidazolidin-4-one

The title compound was prepared by the procedure described in Example 19 using 9.2 g of N-ethyl glycine, 10.9 g of 4-trifluoromethoxyphenyl-isothiocyanate, 10.1 g of triethylamine, and 150 mL of methylene chloride. Purification was achieved by flash chromatography on silica gel (methylene chloride). Title compound (4.6 g) was obtained as a creamy solid, m.p. 116°–119° C. Anal. Calcd. for. $C_{12} H_{11} F_3 N_2 O_2 S$: C, 47.37; H, 3.64; N, 9.21. Found: C, 47.20; H, 3.50; N, 9.13. Mass spectrum (EI, M.$^+$) m/z 304.

EXAMPLE 21

3-(2,6-Dimethylphenyl)-1-ethyl-2-thioxo-imidazolidin-4-one

The title compound was prepared by the procedure described in Example 19 using 9.2 g of N-ethyl glycine, 8.2 g of 2,6-dimethylphenyl-isothiocyanate, 10.1 g of triethylamine, and 150 mL of methylene chloride. Purification was achieved through crystallization from ethanol. Title compound (2.3 g) was obtained as a white solid (2.3 g). m.p. 128°–131° C. Anal. Calcd. for. $C_{13} H_{16} N_2 O S$: C, 62.87; H, 6.49; N, 11.28. Found: C, 62.83; H, 6.50; N, 11.25. Mass spectrum (EI, M.$^+$) m/z 248.

EXAMPLE 22

1-Ethyl-3-(4-fluorobenzyl)-2-thioxo-imidazolidin-4-one

The title compound was prepared by the procedure described in Example 19 using 9.2 g of N-ethyl glycine, 8.4 g of 4-fluorobenzyl-isothiocyanate, 10.1 g of triethylamine, and 150 mL of methylene chloride. Purification was achieved through crystallization from ethyl acetate/hexane mixture. Title compound (4.85 g) was obtained as a white solid, m.p. 73°–76° C. Anal. Calcd. for. $C_{12} H_{13} F N_2 O S$: C, 57.12; H, 5.19; N, 11.10 Found: C, 56.97; H,5.15; N, 11.06. Mass spectrum (EI, M.$^+$) m/z 252.

EXAMPLE 23

1-Ethyl-3-isobutyl-2-thioxo-imidazolidin-4-one

The title compound was prepared by the procedure described in Example 19 using 9.2 g of N-ethyl glycine, 5.7 g of isobutyl-isothiocyanate, 10.1 g of triethylamine, and 150 mL of methylene chloride. Purification was achieved by flash chromatography on silica gel (methylene chloride). Title compound (2.3 g) was obtained as an oil. Anal. Calcd. for. $C_9 H_{16} N_2 O S$: C, 53.97; H, 8.05; N, 13.99. Found: C, 54.01; H, 8.21; N, 14.00) Mass spectrum (EI, M.$^+$) m/z 200.

EXAMPLE 24

3-(2-Chlorophenyl)-1-ethyl-2-thioxo-imidazolidin-4-one

The title compound was prepared by the; procedure described in Example 19 using 9.2 g of N-ethyl glycine, 8.48 g of 2-chlorophenyl-isothiocyanate, 10.1 g of triethylamine, and 150 mL of methylene chloride. Purification was achieved through crystallization from ethanol. Title compound (3.85 g) was obtained as an orange solid, m.p. 142°–145° C. Anal. Calcd. for. $C_{11} H_{11} Cl N_2 O S$: C, 51.87; H, 4.35; N, 11.00. Found: C, 51.96; H, 4.26; N, 10.97. Mass spectrum (EI, M.$^+$) m/z 254.

EXAMPLE 25

1-Ethyl-3-(2-tolyl)-2-thioxo-imidazolidin-4-one

The title compound was prepared by the procedure described in Example 19 using 9.2 g of N-ethyl glycine, 7.4 g of 2-tolyl-isothiocyanate, 10.1 g of triethylamine, and 150 mL of methylene chloride. Purification was achieved through crystallization from ethanol. Title compound (3.6 g) was obtained as a creamy solid, m.p. 105°–108° C. Anal. Calcd. for. $C_{12} H_{14} N_2 O S$: C, 61.51; H, 6.02; N, 11.93. Found: C, 61.22; H, 5.96; N, 11.89. Mass spectrum (EI, M.$^+$) m/z 234.

EXAMPLE 26

1-Ethyl-3-(naphthalen-2-yl)-2-thioxo-imidazolidin-4-one

The title compound was prepared by the procedure described in Example 19 using 9.2 g of N-ethyl glycine, 9.3 g of 2-naphthyl-isothiocyanate, 10.1 g of triethylamine, and 150 mL of methylene chloride. Purification was achieved through crystallization from ethanol. Title compound (4.7 g) was obtained as a light pink solid, m.p. 156°–159° C. Anal. Calcd. for. $C_{15} H_{14} N_2O S$: C, 66.64; H, 5.22; N, 10.36 Found: C, 66.69; H,5.24; N, 10.42. Mass spectrum (EI, M.$^+$) m/z 270.

EXAMPLE 27

3-(2-Chloro-6-methylphenyl)-1-ethyl-2-thioxo-imidazolidin-4-one

The title compound was prepared by the procedure described in Example 19 using 9.2 g of N-ethyl glycine, 9.1 g of 2-chloro-6-methylphenyl-isothiocyanate, 10.1 g of triethylamine, and 150 mL of methylene chloride. Purification was achieved by flash chromatography on silica gel (methylene chloride). Crystallization from ethanol afforded the title compound (5.4 g) as a creamy solid, m.p. 124°–126° C. Anal. Calcd. for. $C_{12} H_{13}$ Cl $N_2$ O S: C, 53.63; H, 4.87; N, 10.42. Found: C, 53.43; H, 4.79; N, 10.28. Mass spectrum (EI, M.$^+$) m/z 268/270.

EXAMPLE 28

1-Ethyl-3-(5-fluoro-2-methylphenyl)-2-thioxo-imidazolidin-4-one

A mixture of the crude N-ethyl glycine (11.5 g), 5-fluoro-2-methylphenylisothiocyanate (10.42 g), triethylamine (12.5 g) and chloroform (300 mL) was heated at reflux for 6 hours. The solvent was evaporated. The residue was dissolved in ethyl acetate (500 mL) and washed with water (500 mL). The organic phase was evaporated to dryness. The residue was dissolved in ethanol (50 mL), then diluted with diethyl ether (200 mL). The solution was saturated with hydrogen chloride. The mixture was filtered. The solid was discarded. The filtrate was evaporated to dryness. The residue was dissolved in diethyl ether (300 mL) and washed with water (200 mL). The organic phase was dried over anhydrous sodium sulfate and evaporated to dryness. Crystallization from ethanol afforded the title compound (6.5 g) as a pink solid, m.p. 98°–100° C. Anal. Calcd. for. $C_{12} H_{13}$ F $N_2O$ S: C, 57.13; H, 5.19; N, 11.10. Found: C, 56.88; H, 5.17; N, 11.05. Mass spectrum (EI, M.$^+$) m/z 252.

EXAMPLE 29

3-(2,6-Diisopropylphenyl)-1-ethyl-2-thioxo-imidazolidin-4-one

The title compound was prepared by the procedure described in Example 16 using 21.9 g of 2,6-diisopropylphenyl-isothiocyanate, 18.4 g of N-ethyl glycine, 20.2 g of triethyl amine, and 300 mL of chloroform. Purification was achieved through crystallization from ethanol. The title compound (8.2 g) was obtained as light yellow solid, m.p. 159°–161° C. Anal. Calcd. for. $C_{17} H_{24} N_2O$ S: C, 67.07; H, 7.94; N, 9.20. Found: C, 66.92; H, 8.03; N, 9.13. Mass spectrum (PBEI, M.$^+$) m/z 304.

EXAMPLE 30

1-Ethyl-2-thioxo-3-(2-trifluoromethylphenyl)-imidazolidin-4-one.

The title compound was prepared by the procedure described in Example 19 using 9.2 g of N-ethyl glycine, 10.2 g of 2-(trifluoromethyl)-phenyl-isothiocyanate, 10.1 g of triethylamine, and 150 mL of methylene chloride. The residue was further purified by flash chromatography on silica gel (methylene chloride). Crystallization from ethanol afforded the title compound (2.7 g), m.p. 82°–85° C. Anal. Calcd. for. $C_{12} H_{11} F_3 N_2O$ S: C, 50.00; H, 3.85; N,9.72. Found: C, 50.00; H, 3.61; N, 9.61. Mass spectrum (EI, M.$^+$) m/z 288.

EXAMPLE 31

1-Ethyl-3-(2-ethyl-6-isopropylphenyl)-2-thioxo-imidazolin-4-one

The title compound was prepared by the procedure described in Example 28 using 20.5 g of 2-ethyl-6-isopropylphenyl-isothiocyanate, 18.4 g of N-ethyl glycine, 20.2 g of triethyl amine, and 300 mL of chloroform. Purification was achieved by flash chromatography on silica gel (5–10 % ethyl acetate in hexane). Crystallization from diethyl ether/ hexane afforded pure title compound (7.5 g) as a white solid, m.p. 77°–79° C. Anal. Calcd. for. $C_{16} H_{22} N_2$ O S: C, 66.17; H, 7.64; N, 9.65. Found: C, 66.12; H, 7.77; N, 9.69. Mass spectrum i2EI, M.$^+$) m/z 290.

EXAMPLE 32

1-Ethyl-3-(2-methylphenyl)-2-thioxo-imidazolidin-4-one

The title compound was prepared by the procedure described in Example 28 using 17.7 g of 2-ethyl-6-methylphenyl-isothiocyanate, 18.4 g of N-ethyl glycine, 20.2 g of triethyl amine, and 300 mL of chloroform. The residue was further purified by flash chromatography on silica gel (20% ethyl acetate in hexane).The title compound was obtained (8.6 g) as a light peach solid, m.p. 82°–84° C. Anal. Calcd. for. $C_{14} H_{18} N_2O$ S: C, 64.09; H, 6.92; N, 10.68. Found: C, 64.27; H, 7.04; N, 10.60. Mass spectrum (EI, M.$^+$) m/z 262.

EXAMPLE 33

3-(2-Chloro-4-methylphenyl)-1-ethyl-2-thioxo-imidazolidin-4-one

The title compound was prepared by the procedure described in Example 28 using 18.3 g of 2-chloro-4-methylphenyl-isothiocyanate, 18.4 g of N-ethyl glycine, 20.2 g of triethyl amine, and 300 mL of chloroform. Crystallization from ethyl acetate afforded the title compound (5.8 g) as a peach solid, m.p. 126°–128° C. Anal. Calcd. for. $C_{12} H_{13}$ Cl $N_2O$ S: C, 53.63; H, 4.88; N, 10.42. Found: C, 53.50; H, 4.76; N, 10.28. Mass spectrum (+FAB, IM+H]$^+$) m/z 269/271.

EXAMPLE 34

1-Ethyl-3,[1-(4-fluorophenyl)-ethyl]-2-thioxo-imidazolidin-4-one

The title compound was prepared by the procedure described in Example 16 using 18.1 g of 1-(4-fluorophenyl)-ethyl-isothiocyanate, 18.4 g of N-ethyl glycine, 20.2 g of triethyl amine, and 300 mL of chloroform. Crystallization from ethyl acetate afforded the title compound (8.8 g) as a light yellow solid, m.p. 93°–95° C. Anal. Calcd. for. $C_{13} H_{15}$ F $N_2O$ S: C, 58.63; H, 5.68; N, 10.52. Found: C, 58.69; H, 5.64; N, 10.58. Mass spectrum (El, M.$^+$) m/z 266.

EXAMPLE 35

3-(2,4-Dichlorophenyl)-1-ethyl-2-thioxo-imidazolidin-4-one

The title compound was prepared by the procedure described in Example 16 using 20.4 g of 2,3-dichlorophenyl-isothiocyanate, 18.4 g of N-ethyl glycine, 20.2 g of triethyl amine, and 300 mL of chloroform. Purification was achieved by flash chromatography on silica gel (20% ethyl acetate in hexane) The title compound (8.8 g) was obtained as a light peach solid, m.p. 144°–146° C. Anal. Calcd. for. $C_{11}H_{10}Cl_2N_2O$ S: C, 45.69; H, 3.49; N, 9.69. Found: C, 45.81; H, 3.40; N, 9.58. Mass spectrum (CI, $[M+H]^+$) m/z 289/29 1/293.

EXAMPLE 36

1-Ethyl-3phenethyl-2-thioxo-imidazolidin-4-one

The title compound was prepared by the procedure described in Example 16 using 16.3 g of phenethyl-isothiocyanate, 18.4 g of N-ethyl glycine, 20.2 g of triethyl amine, and 300 m/L of chloroform. Purification was achieved by flash chromatography on silica gel (20% ethyl acetate in hexane) The title compound (15.0 g) was obtained as an off-white solid, m.p. 66°–68° C. Anal. Calcd. for. $C_{13}H_{16}N_2O$ S: C, 62.87; H, 6.49; N, 11.28. Found: C, 63.03; H, 6.49; N, 11.32. Mass spectrum (EI, $M.^+$) m/z 248.

EXAMPLE 37

3-(2,3-Dimethylphenyl)-1-ethyl-2-thioxo-imidazolidin-4-one

The title compound was prepared by the procedure described in Example 16 using 16.3 g of 2,3-dimethylphenyl-isothiocyanate, 18.4 g of N-ethyl glycine, 20.2 g of triethyl amine, and 250 mL of chloroform. Crystallization from ethanol afforded the title compound (10.3 g) as a light pink solid, m.p. 120°–121° C. Anal. Calcd. for. $C_{13}H_{16}N_2O$ S: C, 62.87; H, 6.49; N, 11.28. Found: C, 62.72; H,. 6.44; N, 11.47. Mass spectrum (EI, $M.^+$) m/z 248.

EXAMPLE 38

3-(2,4-Dimethylphenyl)-1-ethyl-2-thioxo-imidazolidin-4-one

The title compound was prepared by the procedure described in Example 16 using 16.3 g of 2,4-dimethylphenyl-isothiocyanate, 18.4 g of N-ethyl glycine, 20.2 g of triethyl amine, and 250 mL of chloroform. Crystallization from ethanol afforded the title compound (10.8 g) as a light peach solid, m.p. 161°–162° C. Anal. Calcd. for. $C_{13}H_{16}N_2O$ S: C,62.87; H, 6.49; N, 11.28. Found: C, 62.63; H, 6.45; N, 11.17. Mass spectrum (EI, $M.^+$) m/z 248.

EXAMPLE 39

3-(2,5-Dimethylphenyl)-1-ethyl-2-thioxo-imidazolidin-4-one

The title compound was prepared by the procedure described in Example 16 using 16.3 g of 2,5-dimethylphenyl-isothiocyanate, 18.4 g of N-ethyl glycine, 20.2 g of triethyl amine, and 250 mL of chloroform. Crystallization from ethyl acetate afforded the title compound (10.6 g) as an off-white solid, m.p. 176°–178° C. Anal. Calcd. for. $C_{13}H_{16}N_2O$ S: C,62.87; H, 6.49; N, 11.28. Found: C, 62.70; H, 6.46; N, 11.27. Mass spectrum (EI, $M.^+$) m/z 248.

EXAMPLE 40

1-Ethyl-2-thioxo-3-(2,4,5-trimethylphenyl)-imidazolidin-4-one

The title compound was prepared by the procedure described in Example 16 using 17.7 g of 2,4,5-trimethylphenyl-isothiocyanate, 18.4 g of N-ethyl glycine, 20.2 g of triethyl amine, and 250 mL of chloroform. Crystallization from ethanol afforded the title compound (15.3g) as an off-white solid, m.p. 162°–164° C. Anal. Calcd. for. $C_{14}H_{18}N_2O$ S: C,64.09; H, 6.92; N, 10.68. Found: C, 64.21; H, 6.93; N, 10.80. Mass spectrum (EI, $M.^+$) m/z 262.

EXAMPLE 41

1-Ethyl-3-(2-isopropyphenyl)-2-thioxo-imidazolidin-4-one

The title compound was prepared by the procedure described in Example 16 using 15.42 g of 2-isopropylphenyl-isothiocyanate, 16.05 g of N-ethyl glycine, 12 g of triethyl amine, and 200 mL of chloroform. Purification was achieved by flash chromatography on silica gel (5–20 % ethyl acetate in hexane) Crystallization from ethanol afforded the title compound (9.8 g) as a white solid, m.p. 125°–127° C. Anal. Calcd. for. $C_{14}H_{18}N_2O$ S: C, 64.09; H, 6.91; N, 10.68. Found: C, 64.19 H, 6.93; N, 10.71. Mass spectrum (EI, $M.^+$) m/z 262.

EXAMPLE 42

1-Ethyl-3-(2-ethyphenyl)-2-thioxo-imidazolidin-4-one

The title compound was prepared by the procedure described in Example 16 using 16.3 g of 2-ethylphenyl-isothiocyanate, 18.4 g of N-ethyl glycine, 20.2 g of triethyl amine, and 200 mL of chloroform. Purification was achieved by flash chromatography on silica gel (5–10 % ethyl acetate in hexane) Crystallization from diethyl ether afforded the title compound (9.12 g) as a white solid, m.p. 71°–73° C. Anal. Calcd. for. $C_{13}H_{16}N_2O$ S: C,62.87; H, 6.49; N, 11.28. Found: C, 62.81; H, 6.43; N, 11.17. Mass spectrum (EI, $M.^+$) m/z 248.

EXAMPLE 43

3-(5-Chloro-2-methylphenyl)-1-phenyl-2-thioxo-imidazolidin-4-one

A mixture of N-phenyl glycine ethyl ester (8.95 g), 5-chloro-2-methylphenylisothiocyanate (9.18 g), and chloroform (200 mL) was heated at reflux for 24 hours. The solvent was evaporated. The residue was crystallized from ethyl acetate/hexane mixture. The solid was collected and dried to give 17.2 g of 2-[3-(5-chloro-2-methylphenyl)-1-phenyl -thioureido]-acetic acid ethyl ester as a white solid, m.p. 148°–150° C. Anal. Calcd. for. $C_{18}H_{19}Cl N_2O$ S: C, 59.58; H, 5.28; N, 7.72. Found: C, 59.79; H, 5.38; N, 7.65. Mass spectrum (EI, $M.^+$) m/z 262/264.

A mixture of 2-[3-(5-chloro-2-methylphenyl)-1-phenyl-thioureido]-acetic acid ethyl ester (9.5 g), triethyl amine (1 mL), and ethanol (150 mL) was heated at reflux for 2 hours. The mixture was concentrated to one-half volume and cooled to ambient temperature. The solid was collected and air dried to give the title compound (6.1 g) as an off-white solid, m.p. 168°–170° C. Anal. Calcd. for. $C_{16}H_{13}Cl N_2O$ S: C, 60.66; H, 4.14; N, 8.84. Found: C, 60.81; H, 4.16; N, 8.81. Mass spectrum (EI, M.$^+$) m/z 316/318.

EXAMPLE 44

3-(3-Chloro-2-methylphenyl)-1-phenyl-2-thioxo-imidazolidin-4-one

A mixture of N-phenyl glycine ethyl ester (8.95 g), 3-chloro-2-methylphenylisothiocyanate (9.18 g), and chloroform (200 mL) was heated at reflux for 18 hours. The solvent was evaporated to dryness. The residue was mixed with ethanol (150 mL), and triethyl amine (3 mL). The mixture was heated at reflux for 3 hours. The solvent was evaporated. The residue was dissolved in ethyl acetate (300 mL) and washed with 1N HCl (2×200 mL), then with water (200 mL). The organic phase was dried over anhydrous magnesium sulfate and evaporated to dryness. The residue was treated with diethyl ether. The solid was collected by filtration and air dried to give the title compound (5.3 g) as an off-white solid, m.p. 154°–156° C. Anal. Calcd. for. $C_{16} H_{13} Cl N_2 O S$: C, 60.66; H, 4.14; N, 8.84. Found: C, 60.48; H, 4.05; N, 8.76. Mass spectrum (+FAB, [M+H]$^+$) m/z 317/319.

EXAMPLE 45

3-(5-Chloro-2-methylphenyl)-1-isopropyl-2-thioxo-imidazolidin-4-one

2-Chloro acetic acid (69.0 g) was added portionwise while stirring to a isopropyl amine (431.5 g). The addition was carried over a period of 30 minutes. The mixture was stirred at ambient temperature for 18 hours. The excess isopropyl amine was evaporated leaving a viscous clear oil (182.0 g) which solidified upon standing. The crude product consisted of a 1:1 mixture of N-isopropyl glycine and isopropyl amine hydrochloride. This product mixture was used without further purification for the preparation of the title compound, in the next paragraph, and for preparation of the title compounds described in Example 46 through Example 52.

A mixture of the crude N-isopropyl glycine (21.2 g), 5-chloro-2-methylphenylisothiocyanate (18.3 g), triethyl amine (21.0 g) and chloroform (300 mL) was heated at reflux for 4 hours. The solvent was evaporated. The residue was dissolved in ethyl acetate (400 mL) and water (300 mL). The organic phase was washed with 2N HCl (2×300 mL), then with water. The organic phase was dried over anhydrous magnesium sulfate and evaporated to dryness. Crystallization from ethanol afforded the title compound (15.4 g) as a peach solid, m.p. 142°–144° C. Anal. Calcd. for. $C_{13} H_{15} Cl N_2 O S$: C, 55.21; H, 5.35; N, 9.91. Found: C, 55.07; H, 5.20; N, 9.82. Mass spectrum (+FAB, [M+H]$^+$) m/z 283/285.

EXAMPLE 46

3-(2,6-Dimethylphenyl)-1-isopropyl-2-thioxo-imidazolidin-4-one

The title compound was prepared by the procedure described in Example 45 using 16.3 g of 2,6-dimethylphenyl-isothiocyanate, 21.2 g of N-isopropyl glycine, 21.0 g of triethyl amine, and 300 mL of chloroform. Crystallization from ethanol afforded the title compound (12.9 g) as a white solid, m.p. 135°–137° C. Anal. Calcd. for. $C_{14} H_{18} N_2 O S$: C, 64.09; H, 6.92; N, 10.68. Found: C, 63.99; H, 6.72; N, 10.67. Mass spectrum (+FAB, I M+H]$^+$) m/z 263.

EXAMPLE 47

3-(2,6-Diisopropylphenyl)-1-isopropyl-2-thioxo-imidazolidin-one

The title compound was prepared by the procedure described in Example 45 using 21.9 g of 2,6-diisopropylphenyloisothiocyanate, 21.2 g of N-isopropyl glycine, 21.0 g of triethyl amine, and 300 mL of chloroform. Crystallization from ethanol afforded the title compound (11.7 g) as a white solid, m.p. 175°–177° C. Anal. Calcd. for. $C_{18} H_{26} N_2 O S$: C, 67.88; H, 8.23; N, 8.80. Found: C, 68.03; H, 8.09; N, 8.81. Mass spectrum (+FAB, [M+H]$^+$) m/z 319.

EXAMPLE 48

3-(4-Fluorophenyl)-1-isopropyl-2-thioxo-imidazolidin-4-one

The title compound was prepared by the procedure described in Example 45 using 15.3 g of 4-fluorophenyl-isothiocyanate,. 21.2 g of N-isopropyl glycine, 21.0 g of triethyl amine, and 300 mL of chloroform. Crystallization from ethanol afforded the title compound (12.6 g) as a peach solid, m.p. 184°–186° C. Anal. Calcd. for. $C_{12} H_{13} F N_2 O S$: C, 57.12; H, 5.19; N, 11.10. Found: C, 56.98; H, 5.09; N, 11.06. Mass spectrum (+FAB, [M+H]$^+$) m/z 253.

EXAMPLE 49

3-(Indan-5-yl)-1-isopropyl-2-thioxo-imidazolidin-4-one

The title compound was prepared by the procedure described in Example 45 using 17.5 g of indan-5-yl-isothiocyanate, 21.2 g of N-isopropyl glycine, 21.0 g of triethyl amine, and 300 mL of chloroform. Crystallization from ethanol afforded the title compound (9.9 g) as a white solid, m.p. 178°–180° C. Anal. Calcd. for. $C_{15} H_{18} N_2 O S$: C, 56.66; H, 6.61; N, 10.21. Found: C, 56.70; H, 6.67; N, 10.22. Mass spectrum (EI, M.$^+$) m/z 274.

EXAMPLE 50

3-(2-Ethyl-6-methylphenyl)-1-isopropyl-2-thioxo-imidazolidin-4-one

The title compound was prepared by the procedure described in Example 45 using 17.7 g of 2-ethyl-6-methylphenyl-isothiocyanate, 21.2 g of N-isopropyl glycine, 21.0 g of triethyl amine, and 300 mL of chloroform. Crystallization from ethanol afforded the title compound (13.0 g) as a light yellow solid, m.p. 132°–134° C. Anal. Calcd. for. $C_{15} H_{20} N_2 O S$: C, 65.18; H, 7.29; N, 10.14. Found: C, 65.06; H, 7.37; N, 10.20. Mass spectrum (EI, M.$^+$) m/z 276.

EXAMPLE 51

3-(2-Ethylphenyl)-isopropyl-2-thioxo-imidazolidin-4-one

The title compound was prepared by the procedure described in Example 45 using 16.3 g of 2-ethylphenyl-isothiocyanate, 21.2 g of N-isopropyl glycine, 21.0 g of triethyl amine, and 300 mL of chloroform. Crystallization from diethyl ether afforded the title compound (6.8 g) as a white solid, m.p. 103°–105° C. Anal. Calcd. for. $C_{14} H_{18} N_2 O S$: C, 64.09; H, 6.92; N, 10.68. Found: C, 64.08; H, 6.92; N, 10.62. Mass spectrum (EI, M.$^+$) m/z 262.

EXAMPLE 52

1-Isopropyl-3-(2-isopropylphenyl)2-thioxo-imidazolidin-4-one

The title compound was prepared by the procedure described in Example 45 using 10.0 g of 2-isopropylphenyl-isothiocyanate, 11.9 g of N-isopropyl glycine, 12.0 g of triethyl amine, and 200 mL of chloroform. Crystallization from ethanol afforded the title compound (6.8 g) as a light pink solid, m.p. 112°–114° C. Anal. Calcd. for. $C_{15} H_{20} N_2O S$: C, 65.18; H, 7.29; N, 10.13, Found: C, 65.51; H, 7.25; N, 10.32. Mass spectrum (EI, M.$^+$) m/z 276.

EXAMPLE 53

1-Benzyl-3-(4-butylphenyl)-2-thioxo-imidazolidin-4-one

A mixture of N-benzyl glycine (8.7 g), 4-n-butylphenyl-isothiocyanate (8.55 g), triethyl amine (5.5 g) and chloroform (150 mL) was heated at reflux for 5 hours. The solvent was evaporated. The residue was dissolved in ethyl acetate (300 mL) and water (2×200 mL). The organic phase was dried over anhydrous magnesium sulfate and evaporated to dryness. Crystallization from ethyl acetate afforded the title compound (11.4 g) as an off-white solid, m.p. 149°–151° C. Anal. Calcd. for. $C_{20} H_{22} N_2O S$: C, 70.97; H, 6.55; N, 8.28. Found: C, 70.81; H, 6.76; N, 8.32. Mass spectrum (EI, M.$^+$) m/z 338.

EXAMPLE 54

1-Butyl-3-(5-chloro-2-methylphenyl)-2-thioxo-imidazolidin-4-one

2-Chloro acetic acid (47.3 g) was added portionwise while stirring to a n-butyl amine (500.0 g). The addition was carried over a period of 30 minutes. The mixture was stirred at ambient temperature for 18 hours. The excess n-butyl amine was evaporated leaving a viscous clear oil (120.0 g) which solidified upon standing. The crude product consisted of a 1:1 mixture of N-butyl glycine and butyl amine hydrochloride. This product mixture was used without further purification for the preparation of the title compound, in the next paragraph, and for preparation of the title compounds described in Example 55 and Example 56.

A mixture of N-butyl glycine (12.0 g), 5-chloro-2-methylphenyl-isothiocyanate (9.15 g), triethyl amine (12.0 g) and chloroform (200 mL) was heated at reflux for 5 hours. The solvent was evaporated. The residue was treated with diethyl ether (400 mL). The mixture was filtered. The solid was washed with diethyl ether then discarded. The filtrate was evaporated to dryness. Crystallization from ethanol afforded the title compound (6.0 g) as a tan solid, m.p. 102°–103° C. Anal. Calcd. for. $C_{14} H_{17} Cl N_2 O S$: C, 56.65; H, 5.77; N, 9.44. Found: C, 56.41; H, 5.97; N, 9.36. Mass spectrum (EI, M.$^+$) m/z 296/298.

EXAMPLE 55

1-Butyl-3-(4-fluorophenyl)-2-thioxo-imidazolidin-4-one

The title compound was prepared by the procedure described in Example 54 using 7.7 g of 4-fluorophenyl-isothiocyanate, 12.0 g of N-butyl glycine, 15.0 g of triethyl amine, and 250 mL of chloroform. Crystallization from ethanol afforded the title compound (5.9 g) as an off-white solid, m.p. 92°–93° C. Anal. Calcd. for. $C_{13} H_{15} F N_2O S$: C, 58.62; H, 5.68; N, 10.52. Found: C, 58.23; H, 5.65; N, 10.56. Mass spectrum (EI, M.$^+$) m/z 266.

EXAMPLE 56

1-Butyl-3-(3-chloro-6-methylphenyl)-2-thioxo-imidazolidin-4-one

The title compound was prepared by the procedure described in Example 54 using 6.5 g of 2-chloro-6-methylphenyl-isothiocyanate, 8.5 g of N-butyl glycine, 10.0 g of triethyl amine, and 150 mL of methylene chloride. Purification was achieved by flash chromatography on silica gel (methylene chloride). Crystallization from ethanol afforded the title compound (3.85 g) as a light pink solid, m.p. 97°–100° C. Anal. Calcd. for. $C_{14} H_{17} Cl N_2O S$: C, 56.65; H, 5.77; N, 9.44. Found: C, 56.45; H, 5.67; N, 9.33. Mass spectrum (+FAB, [M+H]$^+$) m/z 297.

EXAMPLE 57

3-(4-t-Butylphenyl)-1-methyl-2-thioxo-imidazolidin-4-one

A mixture of sarcosine ethyl ester hydrochloride (7.68 g), 4-t-butylphenylisothiocyanate (9.6 g), triethyl amine (10.1 g) and chloroform (250 mL) was heated at reflux for 3 hours. The mixture was cooled to ambient temperature, washed with 2N HCl (2×200 mL), then with water (200 mL). The organic phase was dried over anhydrous magnesium sulfate and evaporated to dryness. The residue was crystallized from ethanol to give the title compound (9.9 g), m.p. 156°–158° C. Anal. Calcd. for $C_{14} H_{18} N_2O S$: C, 64.09; H, 6.91; N,10.68. Found: C, 63.83; H, 7.15; N, 10.53. Mass spectrum (EI, M.$^+$) m/z 262.

EXAMPLE 58

1-Ethyl-3-(2-methylsulfanylphenyl)-2-thioxo-imidazolidin-4-one

A mixture of N-ethyl glycine (9.23 g), 2-(methylthio)-phenyl-isothiocyanate (9.1 g), triethylamine (10.1 g) and methylene chloride (150 mL) was heated at reflux for 3 hours. The mixture was evaporated to dryness. The residue was recrystallized from ethanol to give the title compound (6.5 g) as a creamy solid, m.p. 128°–131° C. Anal. Calcd. for. $C_{12}H_{14}N_2S_2O$: C, 52.11; H, 5.30; N, 10.52. Found: C, 52.28; H, 5.26; N, 10.54. Mass spectrum (EI, M.$^+$) m/z 266.

EXAMPLE 59

1-Allyl-3-(2,6-dimethylphenyl)-2-thioxo-imidazolidin-4-one

Chloroacetic acid (27.5 g) was added portionwise over 5 minutes to a cooled solution of allylamine (114 g) in water (100 mL). The reaction mixture was stirred at ambient temperature for 48 hours. The mixture was then evaporated to a viscous oily residue (35 g). The crude product consisted of a 1:1 mixture of N-allyl glycine and allyl amine hydrochloride. This product mixture was used without further purification for the preparation of the title compound, in the next paragraph, and for preparation of the title compound described in Example 60.

A mixture of N-allyl glycine (17.4 g), 2,6-dimethylphenyl-isothiocyanate (20 g), triethylamine (20.2 g), and methylene chloride (150 mL) was heated at reflux for 3 hours. The reaction mixture was evaporated to dryness. The residual gum was dissolved in diethyl ether, then treated with etheral hydrogen chloride. A white solid formed. The solid was filtered and discarded. The filtrate was concentrated to a residue. The residue was chromatographed on silica gel (CH$_2$Cl$_2$) to give title compound (5.2 g) as an orange solid, m.p. 43°–46° C. Anal. Calcd. for. C$_{14}$ H$_{16}$ N$_2$ O S: C, 64.59; H, 6.19; N, 10.76. Found: (2, 64.52; H, 6.08; N, 10.66. Mass spectrum (EI, M.$^+$) m/z 260.

EXAMPLE 60

1-Allyl-3-(5-chloro-2methylphenyl)-2-thioxo-imidazolidin-4-one

A mixture of N-allyl glycine (17.4 g), 5-chloro-2-methylphenyl-isothiocyanate (20.1 g), triethylamine (20.2 g), and methylene chloride (150 mL) was heated at reflux for 2 hours. The reaction mixture was evaporated to dryness. Purification was achieved by flash chromatography on silica gel (methylene chloride). Recrystallization from Hexane-EtOAc afford the title compound (4.8 g) as yellow solid, m.p. 106°–109° C. Anal. Calcd. for. C$_{13}$ H$_{13}$ N$_2$O Cl S: C, 55.61; H, 4.67; N, 9.98. Found: C, 55.45; H, 4.56; N, 9.72. Mass spectrum (EI, M.$^+$) m/z 280.

EXAMPLE 61

3-(2,6-dimethylphenyl)-1-(prop-2-ynyl)-2-thioxo-imidazolidin-4-one

To a cooled solution of ethyl bromoacetate (37.6 g) in diethyl ether (75 mL), was added propargylamine (25 g). The mixture was stirred for 3 hour at 0°–5° C. The reaction temperature was raised to ambient temperature, and the stirring continued for 18 hours. A solid formed. The solid was filtered and discarded. The filtrate was evaporated to dryness to give crude title compound (30.1 g). The crude product was used without further purification for the preparation of the title compound, in the next paragraph, and for preparation of the title compounds described in Example 62 and Example 63.

A mixture of ethyl N-propargylaminoacetate (14.1 g), 2,6-dimethylphenylisothiocyanate (16.3 g), triethylamine (10.1 g), and methylene chloride (150 mL) was heated at reflux for 3 hours. The reaction mixture was cooled to ambient temperature, washed with 1N HCl (100 mL), then with water. The organic layer was separated, dried over anhydrous magnesium sulfate, then evaporated to dryness. The residual oil was triturated with hexane. The solid w, as collected by filtration. Recrystallization from hexane-EtOAc afforded the title compound (12.5 g) as yellow solid, m.p. 117°–121° C. Anal. Calcd. for. C$_{14}$ H$_{14}$N$_2$S$_2$ O: C, 65.09; H, 5.46; N, 10.84. Found: C, 65.23; H, 5.43; N, 10.88. Mass spectrum (EI, M.$^+$) m/z 258.

EXAMPLE 62

3-(5-chloro-2-methylphenyl)-1-(prop-2ynyl)-2-thioxo-imidazolidin-4-one

A mixture of ethyl N-propargylaminoacetate (7.0 g), 5-chloro-2-methylphenylisothiocyanate (9.2 g), triethylamine (5.0 g), and methylene chloride (100 mL) was heated at reflux for 3 hours. The reaction mixture was cooled to ambient temperature, washed with 1 N HCl (50 mL), then with water. The organic layer was dried over anhydrous magnesium sulfate, then evaporated to dryness. The residual oil was triturated with hexane. The solid was collected by filtration. Recrystallization from EtOAc afford the title compound (5.1 g) as yellow solid, m.p. 131°–134° C. Anal. Calcd. for. C$_{13}$ H$_{11}$ N$_2$ O Cl S: C, 56.01; H, 3.98; N, 10.05. Found: C, 55.90; H, 3.77; N, 9.92. Mass spectrum (EI, M.$^+$) m/z 278.

EXAMPLE 63

3-(4-chloro-2-methylphenyl)-1-(prop-2-ynyl)-2-thioxo-imidazolidin-4-one

A mixture of ethyl N-propargylaminoacetate (10.0 g), 4-chloro-2-methylphenylisothiocyanate (12.9 g), triethylamine (7.1 g), and methylene chloride (150 mL) was heated at reflux for 3 hours. The reaction mixture was cooled to ambient temperature, washed with 1 N HCl (100 mL), then with water. The organic layer was dried over anhydrous magnesium sulfate, then evaporated to dryness. The residual oil was triturated with hexane. The solid was collected by filtration. Recrystallization from Hexane-EtOAc afford the title compound (5.2 g) as yellow solid, m.p. 99°–102° C. Anal. Calcd. for. C$_{13}$ H$_{11}$ N$_2$O Cl S: C, 56.01; H, 3.98; N, 10.05. Found: C, 55.61; H, 3.83; N, 10.0. Mass spectrum (EI, M.$^+$) m/z 278.

What is claimed is:

1. A method for increasing the HDL cholesterol concentration in the blood of a mammal in need of increased HDL cholesterol blood concentration, which comprises administering to said mammal, orally or parenterally, a compound of formula I:

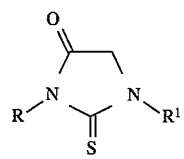

wherein

R is alkyl of 1 to 6 carbon atoms; unsubstituted aromatic N, O or S heterocycle having 4 to 6 carbon and one hetero ring member; substituted or unsubstituted aryl of 6 to 10 carbon atoms, arylalkyl of 7 to 12 carbon atoms, benzhydryl or indanyl, in which the substituents are one to three members independently selected from the group consisting of alkyl of 1 to 6 carbon atoms, alkoxy of 1 to 6 carbon atoms, alkylthio of 1 to 6 carbon atoms, alkenyl of 2 to 6 carbon atoms, alkynyl of 2 to 6 carbon atoms, halo, perfluoroalkyl of 1 to 6 carbon atoms, perfluoroalkoxy of 1 to 6 carbon atoms or hydroxy; and R$^1$ is aryl of 6 to 10 carbon atoms, alkyl of 1 to 6 carbon atoms, alkenyl of 2 to 6 carbon atoms, alkynyl of 2 to 6 carbon atoms or substituted aryl of 6 to 10 carbon atoms where the substituents are one to three members independently selected from the group consisting of alkyl of 1 to 6 carbon atoms, alkoxy of 1 to 6 carbon atoms, alkylthio of 1 to 6 carbon atoms, alkenyl of 2 to 6 carbon atoms, alkynyl of 2 to 6 carbon atoms, halo, perfluoroalkyl of 1 to 6 carbon atoms, perfluoroalkoxy of 1 to 6 carbon atoms or hydroxy.

2. A method of claim 1 in which said compound administered is of formula I in which R is substituted phenyl where the substituents are two members of the group consisting of alkyl of 1 to 6 carbon atoms, perfluoroalkoxy of 1 to 6 carbon atoms, halo, or ortho substituted trimethylene or tetramethylene and R$^1$ is alkyl of 1 to 6 carbon atoms, alkenyl of 2 to 6 carbon atoms or alkynyl of 2 to 6 carbon atoms.

3. A method of claim 1 in which said compound administered is of formula I in which R is substituted phenyl where the substituents are a halo and an alkyl group of 1 to 3 carbon atoms or ortho substituted trimethylene and. $R^1$ is alkyl of 1 to 3 carbon atoms, alkenyl of 2 to 4 carbon atoms or alkynyl of 2 to 4 carbon atoms.

4. A method of claim 1 in which said compound administered is of formula I in which R is substituted phenyl where the substituents are chloro or fluoro in the 4- or 5-position and an alkyl group of 1 to 3 carbon atoms and $R^1$ is alkyl of 1 to 3 carbon atoms, alkenyl of 2 to 4 carbon atoms or alkynyl of 2 to 4 carbon atoms.

5. The method of claim 1 in which said compound is selected from the group consisting of:
3-(5-Chloro-2-methylphenyl)-1-methyl-2-thioxo-imidazolidin-4-one;
3-(3-Chloro-2-methylphenyl)-1-methyl-2-thioxo-imidazolidin-4-one;
3-(4-Chloro-2-methylphenyl)-1-methyl-2-thioxo-imidazolidin-4-one;
3-(Indan-5-yl)-1-methyl-2-thioxo-imidazolidin-4-one;
3-(2,6-Diisopropylphenyl)-1-methyl-2-thioxo-imidazolidin-4-one;
3-(2-Ethyl-6-isopropylphenyl)-1-methyl-2-thioxo-imidazolidin-4-one;
3-(2-Ethyl-6-methylphenyl)-1-methyl-2-thioxo-imidazolidin-4-one;
3-(5-Chloro-2-methylphenyl)-1-ethyl-2-thioxo-imidazolidin-4-one;
3-(2,6-Dichlorophenyl)-1-ethyl-2-thioxo-imidazolidin-4-one;
1-Ethyl-3-(4-fluorophenyl)-2-thioxo-imidazolidin-4-one;
1-Ethyl-2-thioxo-3-(4-trifluoromethoxyphenyl)-imidazolidin-4-one;
3-(2,6-Dimethylphenyl)-1-ethyl-2-thioxo-imidazolidin-4-one;
1-Ethyl-3-isobutyl-2-thioxo-imidazolidin-4-one;
3-(2-Chlorophenyl)-1-ethyl-2-thioxo-imidazolidin-4-one;
1-Ethyl-3-(2-tolyl)-2-thioxo-imidazolidin-4-one;
3-(2-Chloro-6-methylphenyl)-1-ethyl-2-thioxo-imidazolidin-4-one;
1-Ethyl-3-(5-fluoro-2-methylphenyl)-2-thioxo-imidazolidin-4-one;
3-(2,6-Diisopropylphenyl)-1-ethyl-2-thioxo-imidazolidin-4-one;
1-Ethyl-2-thioxo-3-(2-trifluoromethylphenyl )-imidazolidin-4-one;
1-Ethyl-3-(2-chloro-6-methylphenyl)-2-thioxo- imidazolidin-4-one;
3-(2-Ethyl-4-methylphenyl)-1-ethyl-2-thioxo-imidazolidin-4-one;
3-(2,4-Dichlorophenyl)-1-ethyl-2-thioxo-imidazolidin-4-one;
3-(2,4-Dimethylphenyl)-1-ethyl-2-thioxo-imidazolidin-4-one;
3-(2,5-Dimethylphenyl)-1-ethyl-2-thioxo-imidazolidin-4-one;
1-Ethyl-2-thioxo-3-(2,4,5-trimethylphenyl)-imidazolidin-4-one;
1-Ethyl-3-(2-isopropylphenyl)-2-thioxo-imidazolidin-4-one;
1-Ethyl-3-(2-ethylphenyl)-2-thioxo-imidazolidin-4-one;
3-(5-Chloro-2-methylphenyl)-1-phenyl-2-thioxo-imidazolidin-4-one;
3-(5-Chloro-2-methylphenyl)-1-isopropyl-2-thioxo-imidazolidin-4-one;
3-(2,6-Dimethylphenyl)-1-isopropyl-2-thioxo-imidazolidin-4-one;
3-(2-Ethyl-6-methylphenyl)-1-isopropyl-2-thioxo-imidazolidin-4-one;
1-Butyl-3-(4-fluorophenyl)-2-thioxo-imidazolidin-4-one;
1-Allyl-3-(2,6-dimethylphenyl)-2-thioxo-imidazolidin-4-one;
3-(2,6-Dimethylphenyl)-1-(prop-2-ynyl)-2-thioxo-imidazolidin-4-one;
3-(3-Chloro-4-methylphenyl )-1-methyl-2-thioxo-imidazolidin-4-one
3-(2-Ethylphenyl)-1-methyl-2-thioxo-imidazolidin-4-one
1-Methyl-3-(2-isopropylphenyl )-2-thioxo-imidazolidin-4-one
3-(4-t-Butylphenyl)-1-methyl-2-thioxo-imidazolidin-4-one
1-Allyl-3-(5-chloro-2-methylphenyl)-2-thioxo-imidazolidin-4-one
3-(5-Chloro-2-methylphenyl)-1-(prop-2-ynyl)-2-thioxo-imidazolidin-4-one; or
1-Ethyl-3-(2-ethyl-6-isopropylphenyl)-2-thioxo-imidazolidin-4-one.

6. The method of claim 1 in which said compound is 3-(5-chloro-2-methylphenyl)-1-methyl-2-thioxo -imidazolidin-4-one.

7. The method of claim 1 in which said compound is 3-(3-chloro-2-methylphenyl)-1-methyl-2 -thioxo-imidazolidin-4-one.

8. The method of claim 1 in which said compound is 3-(4-chloro-2-methylphenyl)-1-methyl-2 -thioxo-imidazolidin-4-one.

9. The method of claim 1 in which said compound is 3-(2-chloro-6-methylphenyl)-1-methyl-2 -thioxo-imidazolidin-4-one.

10. The method of claim 1 in which said compound is 3-(2-ethylphenyl)-1-methyl-2-thioxo-imidazolidin-4-one.

11. The method of claim 1 in which said compound is 1-methyl-3-(2-isopropylphenyl)-2-thioxo-imidazolidin -4-one.

12. The method of claim 1 in which said compound is 1-ethyl-2-thioxo-3-(4-trifluoromethoxyphenyl)-imidazolidin -4-one.

13. The method of claim 1 in which said compound is 3-(2,6-dimethylphenyl)-1-ethyl-2-thioxo-imidazolidin -4-one.

14. The method of claim 1 in which said compound is 3-(2-chlorophenyl)-1-ethyl-2-thioxo-imidazolidin-4-one.

15. The method of claim 1 in which said compound is 1-ethyl-3-(2-tolyl)-2-thioxo-imidazolidin-4-one.

16. The method of claim 1 in which said compound is 3-(2-chloro-6-methylphenyl)-1-ethyl-2 -thioxo-imidazolidin-4-one.

17. The method of claim 1 in which said compound is 1-ethyl-3-(2-isopropylphenyl)-2-thioxo-imidazolidin -4-one.

18. The method of claim 1 in which said compound is 1-ethyl-3-(2-ethylphenyl)-2-thioxo-imidazolidin-4-one.

19. The method of claim 1 in which said compound is 3-(5-chloro-2-methylphenyl)-1-isopropyl-2-thioxo -imidazolidin-4-one.

20. The method of claim 1 in which said compound is 3-(4-t-butylphenyl)-1-methyl-2-thioxo-imidazolidin -4-one.

21. The method of claim 1 in which said compound is 1-allyl-3-(2,6-dimethylphenyl)-2-thioxo-imidazolidin -4-one.

22. The method of claim 1 in which said compound is 3-(2,6-dimethylphenyl)-1-(prop-2-ynyl)-2-thioxo -imidazolidin-4-one.

23. The method of claim 1 in which said compound is 3-(5-chloro-2-methylphenyl)-1-methyl-2-thioxo -imidazolidin-4-one.

24. The method of claim 1 in which said compound is 3-(5-chloro-2-methylphenyl)-1-ethyl-2-thioxo-imidazolidin-4-one.

25. The method of claim 1 in which said compound is 1-butyl-3-(4-fluorophenyl)-2-thioxo-imidazolidin-4-one.

26. The method of claim 1 in which said compound is 1-ethyl-3-isobutyl-2-thioxoimidazolidin-4-one.

27. The method of claim 1 in which said compound is 3-(3-chloro-4-imidazolidin-4-one.

28. The method of claim 1 in which said compound is 1-ethyl-3-(5-fluoro-2-methylphenyl)-2-thioxo-imidazolidin-4-one.

29. The method of claim 1 in which said compound is 3-(5-chloro-2-methylphenyl)-1-(prop-2-ynyl)-2-thioxo-imidazolidin-4-one.

30. The method of claim 1 in which said compound is 1-Allyl-3-(5-chloro-2-methylphenyl)-2-thioxo-imidazolidin-4-one.

31. The method of claim 1 in which said compound is 3-(2,4-dimethylphenyl)-1-ethyl-2-thioxo-imidazolidin-4-one.

32. The method of claim 1 in which said compound is 1-ethyl-3-(2-ethyl-6-isopropylphenyl)-2-thioxo-imidazolidin-4-one.

33. The method of claim 1 in which said compound is 3-(2-ethyl-6-isopropylphenyl)-1-methyl-2-thioxo-imidazolidin-4-one.

34. The method of claim 1 in which said compound is 1-ethyl-2-thioxo-3-(2,4,5-trimethylphenyl)-imidazolidin-4-one.

35. The method of claim 1 in which said compound is 1-ethyl-3-(2-isopropylphenyl)-2-thioxo-imidazolidin-4-one.

36. The method of claim 1 in which said compound is 3-(2,6-dimethylphenyl)-1-methyl-2-thioxo-imidazolidin-4-one.

* * * * *